(12) United States Patent
Kontaxis et al.

(10) Patent No.: US 9,919,166 B2
(45) Date of Patent: Mar. 20, 2018

(54) IMAGE-GUIDED RADIATION THERAPY

(71) Applicant: Elekta AB (Publ), Stockholm (SE)

(72) Inventors: Charis Kontaxis, Utrecht (NL);
Gijsbert Herman Bol, Utrecht (NL);
Bas Willem Raaymakers, Utrecht (NL)

(73) Assignee: Elekta AB (Publ), Stockholm (SE)

(*) Notice: Subject to any disclaimer, the term of this patent is extended or adjusted under 35 U.S.C. 154(b) by 0 days.

(21) Appl. No.: 15/301,887

(22) PCT Filed: Apr. 7, 2015

(86) PCT No.: PCT/EP2015/057513
§ 371 (c)(1),
(2) Date: Oct. 4, 2016

(87) PCT Pub. No.: WO2015/150575
PCT Pub. Date: Oct. 8, 2015

(65) Prior Publication Data
US 2017/0028221 A1 Feb. 2, 2017

(30) Foreign Application Priority Data

Apr. 4, 2014 (GB) .................................. 1406134.5
May 19, 2014 (GB) .................................. 1408864.5
Oct. 23, 2014 (GB) .................................. 1418868.4

(51) Int. Cl.
*A61N 5/10* (2006.01)
*G21K 5/04* (2006.01)

(52) U.S. Cl.
CPC .......... *A61N 5/1067* (2013.01); *A61N 5/1031* (2013.01); *A61N 5/1037* (2013.01);
(Continued)

(58) Field of Classification Search
CPC .. A61N 5/1067; A61N 5/1047; A61N 5/1031; A61N 5/1039; A61N 5/1071;
(Continued)

(56) References Cited

U.S. PATENT DOCUMENTS 5,661,773 A * 8/1997 Swerdloff ............ A61N 5/1042
378/65
5,818,902 A 10/1998 Yu
(Continued)

FOREIGN PATENT DOCUMENTS

WO WO 2002/049044 A2 6/2002
WO WO 2006/030181 A1 3/2006

OTHER PUBLICATIONS

International Search Report and Written Opinion in International Application PCT/EP2015/057513, dated May 26, 2015.
(Continued)

*Primary Examiner* — Nicole Ippolito
(74) *Attorney, Agent, or Firm* — Finnegan, Henderson, Farabow, Garrett & Dunner LLP

(57) ABSTRACT

The disclosed systems and methods for Image-Guided Radiation Therapy (IGRT), utilizes an iterative approach which adjusts a treatment plan based on inter- or intra-fraction images to improve the accuracy of the radiation delivered during the overall treatment. The prescribed dose of radiotherapeutic radiation is mapped onto the patient's anatomy using an image acquired of the region, which is to be the target for radiotherapeutic radiation. Following beam-angle-optimization, fluence optimization and segmentation, the efficiency of delivery of each segment is determined using an objective function, and the segments ranked according to their efficiency. The plan proceeds with the choice of the most efficient segment (or segments) to be delivered first. When this radiation has been delivered, having been tracked to establish its distribution, this deliv-
(Continued)

ered distribution can be subtracted from the original prescribed dose and the process repeated so that the delivered radiation gradually converges on the original prescribed dose.

38 Claims, 2 Drawing Sheets

(52) U.S. Cl.
CPC ......... *A61N 5/1038* (2013.01); *A61N 5/1039* (2013.01); *A61N 5/1047* (2013.01); *A61N 5/1049* (2013.01); *A61N 5/1071* (2013.01); *A61N 2005/1034* (2013.01); *A61N 2005/1054* (2013.01); *A61N 2005/1055* (2013.01); *A61N 2005/1058* (2013.01)

(58) Field of Classification Search
CPC ................ A61N 5/1038; A61N 5/1049; A61N 2005/1035; A61N 2005/1034; A61N 2005/1054; A61N 2005/1055; A51N 2005/1049

USPC ............ 600/1; 250/492.1, 492.3, 396 R, 397
See application file for complete search history.

(56) References Cited

U.S. PATENT DOCUMENTS

| | | | |
|---|---|---|---|
| 2011/0085643 A1* | 4/2011 | Zhu ..................... | A61N 5/1031 378/65 |
| 2013/0197878 A1* | 8/2013 | Fiege ................... | A61N 5/1031 703/2 |
| 2015/0071408 A1* | 3/2015 | Ebstein ................ | A61N 5/1075 378/65 |

OTHER PUBLICATIONS

Galvin et al., "Combining multileaf fields to modulate fluence distributions," Intl. Journal of Radiation Oncology, Biology, and Physics, vol. 27:3. Oct. 20, 1993, pp. 697-705.

Melado et al., "Fixed number of segments in unidirectional decompositions of fluence matrices for step-and-shoot IMRT," Phys. Med. Biol., vol. 56:8, Mar. 28, 2011, pp. 2601-2615.

* cited by examiner

| 7 | 7 | 7 | 6 | 5 | 4 |
|---|---|---|---|---|---|
| 3 | 8 | 8 | 7 | 4 | 4 |
| 2 | 6 | 10 | 10 | 4 | 4 |
| 2 | 6 | 10 | 10 | 4 | 2 |
| 1 | 3 | 5 | 6 | 2 | 1 |
35  37
Fig. 2
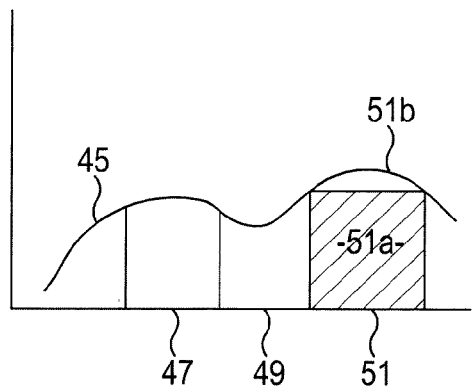
Fig. 3a
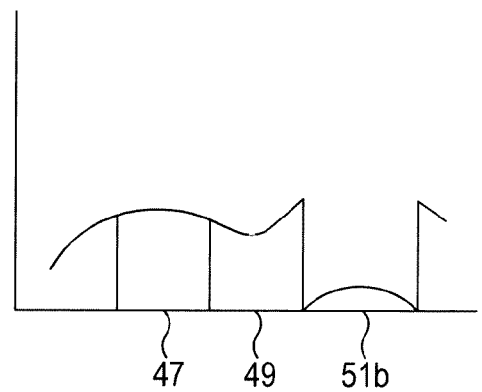
Fig. 3b
Fig. 4a
Fig. 4b

IMAGE-GUIDED RADIATION THERAPY

CROSS-REFERENCE TO RELATED APPLICATION

This application is a national phase of International Application No. PCT/EP2015/057513, filed on Apr. 7, 2015, which claims priority to GB Application No. 1418868.4, filed on Oct. 23, 2014, to GB Application No. 1408864.5, filed on May 19, 2014, and to GB Application No. 1406134.5, filed on Apr. 4, 2014. The contents of the above-referenced applications are expressly incorporated herein by reference in their entireties.

FIELD OF THE INVENTION

The present invention relates to systems and methods for Image-Guided Radiation Therapy (IGRT), particularly but not exclusively when practised with a magnetic resonance imaging (MRI) system, such as an MRI/Linear Accelerator, or "MRL".

BACKGROUND ART

IGRT is the process of frequent two and/or three-dimensional imaging, during radiation treatment, used to direct the delivery of the therapeutic radiation.

It is known that exposure of human or animal tissue to ionising radiation will damage the cells thus exposed. This finds application in the treatment of pathological cells, for example. In order to treat tumours deep within the body of the patient, the radiation must however penetrate the healthy tissue in order to irradiate and destroy the pathological cells. In conventional radiation therapy, large volumes of healthy tissue can thus be exposed to harmful doses of radiation, potentially resulting in unacceptable side-effects. It is therefore desirable to design a system for treating a patient with ionising radiation and treatment protocols so as to expose the pathological tissue to a dose of radiation which will result in the death of those cells, whilst keeping the exposure of healthy tissue to a minimum.

Several methods have previously been employed to achieve the desired pathological cell-destroying exposure whilst keeping the exposure of healthy cells to a minimum. Many methods work by directing radiation at a tumour from a number of directions, either simultaneously from multiple sources or multiple exposures over time from a single movable source. The dose deposited from each direction is therefore less than would be required to destroy the tumour, but where the radiation beams from the multiple directions converge, the total dose of radiation is sufficient to be therapeutic. By providing radiation from multiple directions, the damage caused to surrounding healthy cells can be reduced.

Intensity modulated arc therapy (IMAT) is one method of achieving this, and is described in U.S. Pat. No. 5,818,902. In this process, the radiation source is rotated around the patient, and the radiation beam collimated to take a desired shape depending on the angle of rotation of the source, usually with a multi-leaf collimator (MLC). The potential advantages of a particular form of IMAT, volumetric modulated arc therapy (VMAT), have recently given rise to a number of commercial implementations and research studies. In these systems, the dose rate, rotation speed and MLC leaf positions may all vary during delivery. In general, plans comparable in quality and accuracy to static-gantry intensity-modulated radiotherapy (IMRT) can be obtained, normally with reduced delivery times.

In typical IMRT methods, a linear accelerator rotates on a gantry around the patient, emitting "modulated" beams of X-rays from a number of pre-fixed angles, where modulation is carried out using a multi-leaf collimator (MLC) attached to the head of the linear accelerator. The MLC shapes the pattern of the outgoing radiation beam, through a sequence of movements of its metal leaves, in order to precisely target the tumours while minimizing exposure of the neighbouring healthy structures.

To make sure the radiation beams are correctly directed, the treatment can be guided by imaging of the target region, before or even during a course of radiation treatment—although the latter is usually predicated on a system where a course of treatment is divided into individual treatments (called "fractions", where a treatment is applied on a single day, for example), and imaging is carried out between fractions. This is known as IGRT; a typical IGRT method might include localization of a cone-beam computed tomography (CBCT) dataset with the planning computed tomography (CT) dataset from planning. IGRT might also include matching planar kilovoltage (kV) radiographs or megavoltage (MV) images with digital reconstructed radiographs (DRRs) from the planning CT.

Kilovoltage computational tomography (CT) is carried out during treatment by providing a separate source of imaging radiation mounted on the rotatable gantry, placed at an angle relative to the main radiation head. A detector is positioned diametrically opposite the source of imaging radiation, and collects imaging data for a plurality of rotational angles of the gantry. This data can then be reconstructed to form three-dimensional images using known CT techniques. See PCT application WO 2006/030181 for an example of this method. Kilovoltage radiation is often preferred for imaging due to the high contrast between different structures in the patient.

In megavoltage computational tomography (CT), a radiation detector is placed on the rotatable gantry diametrically opposite the main treatment head, and is designed to detect the megavoltage radiation after it has passed through (and been attenuated by) the patient. The images generated are therefore individual transmission images, from the beam's eye view (BEV). Megavoltage imaging can be used to verify the position of the MLC leaves in relation to the target within the patient. The detector is usually known as an 'electronic portal imaging device' or EPID. However, the high energy associated with therapeutic radiation is not ideal for imaging purposes as the attenuation coefficients of the various tissue types within a patient are similar at this energy level, leading to poor image contrast. In addition, this method is inherently two-dimensional because in conventional radiotherapy the megavoltage beams are directed at the patient from typically at least three angles, which may be insufficient to provide three-dimensional imaging.

The above two methods comprise the majority of IGRT strategies currently employed. However, radiation therapy systems which incorporate real-time MRI tracking of tumours or other radiation targets are currently being developed. One problem with existing and planned radiotherapy systems is to ensure that the radiation distribution is applied accurately according to the treatment plan, in terms of both the locations the radiation is delivered to and the amount of radiation delivered (the "dose") to any particular location. A second problem is that of beam-angle optimisation, which is to determine the "optimal" number and values of gantry angles, which is often formulated as a combinatorial optimisation problem. Another, interrelated problem is to reduce the amount of radiation, or dose, applied to non-targeted tissue which is adjacent to targeted tissue and/or in the path of radiation beams applied to targeted tissue. In addition, each treatment should be delivered in a short time, to minimise the effects of patient or target movement and also to maximise the use of the radiotherapy system. These non-trivial problems are rendered even more complex by practical issues such as the characteristics and/or limitations of the radiotherapeutic and the imaging systems, the accurate positioning of the patient and the target tissue before treatment and the possibility of there being movement of both of these, both inter- and intra-treatment, and inter- and intra-fraction. Computerised treatment planning systems attempt to address these problems, however the computational methods and algorithms used are extremely complex and involve enormous amounts of data to be manipulated, which requires large amounts of processing and takes a significant amount of time. Research continues into methods of delivering radiation in such a way that the dose distribution is accurate (i.e. ensuring that the radiation is delivered to the intended locations, or target region(s), and not to other locations) whilst ensuring careful control of the absolute dose delivered to any single location (i.e. ensuring that the amount of radiation delivered to a target region is in accordance with the treatment plan—at or up to a certain level in the case of a tumour, below a predetermined safe level in the case of non-targeted but non-sensitive tissue, and at a negligible level in the case of certain sensitive, non-targeted tissue).

In the IMRT planning process there are further problems which also need to be considered, all to do with optimisation. One is called the fluence optimisation problem, which is to find a set of "optimal" intensity profiles corresponding to the given set of beam angles. Another is the leaf sequencing problem which is to determine an "optimal" sequence of MLC leaf movements that delivers the intensity profile for each beam angle.

SUMMARY OF THE INVENTION

The present invention utilises an iterative approach which adjusts a treatment plan based on inter- or intra-fraction images to significantly improve the accuracy of the radiation delivered during the overall treatment. The prescribed dose of radiotherapeutic radiation to be delivered during a fraction is mapped onto the patient's anatomy using an image acquired of the region which is to be the target for radiotherapeutic radiation. Following beam-angle-optimisation, fluence optimisation and segmentation, the efficiency of delivery of each segment is determined using an objective function, and the segments ranked according to their efficiency. The plan proceeds with the choice of the most efficient segment (or segments) to be delivered first. When this radiation has been delivered, having been tracked to establish its dose distribution, this delivered dose distribution can be subtracted from the original prescribed dose and the process repeated so that the delivered radiation dose gradually converges on the original prescribed dose. An important advantage of the invention is that it enables radiation to be delivered with great accuracy to a determined, target region; although this may be achieved at the cost of slightly under-irradiating parts of a target region, this can be accurately determined and the part of the prescribed dose which remains undelivered at the end of a treatment, or "missed" radiation, can be accounted for by appropriate adjustment of the dose prescribed for the next treatment in the course. Rather than knowing the absolute level of radiotherapeutic radiation applied and accepting that some (usually a small amount) of that radiation might be distributed outside the desired target region, as is the case in many known techniques, the present invention allows the distribution of the radiation during each fraction to be extremely accurate but accepts that there will usually be a degree of under-irradiation, which is acceptable as it can be compensated for in a subsequent fraction.

The present invention therefore provides, in one aspect, a radiotherapeutic apparatus for delivering a prescribed dose of radiotherapeutic radiation to a target region of patient tissue comprising a source for producing a directable beam of therapeutic radiation, wherein an image depicting patient anatomical data of at least the target region has been acquired and the prescribed dose has been mapped onto the image as the desired dose distribution to be achieved in the target region, the apparatus being adapted and configured to:

a) determine at least one beam angle corresponding to a direction from which the radiotherapeutic radiation is to be delivered from the source to the target region, and for each beam angle create a mask defining a beam outline which substantially matches an outline of the target region as seen from each beam angle;

b) discretize the or each beam within its beam outline into a plurality of pencil beams;

c) for each beam angle carry out a fluence optimisation process using pencil beam data from step b) and patient anatomical and target region data from the image to generate a distribution profile for a sub-dose to be delivered at that beam angle, the separate sub-doses from all the angles in combination substantially equalling the prescribed dose;

d) segment each sub-dose distribution profile into segments, each segment comprising a plurality of pencil beams of matching fluence;

e) determine the efficiency of all of the segments;

f) deliver radiation in accordance with at least one of the most efficient segments of therapeutic radiation;

g) track the radiation delivered in step f) to calculate the amount and distribution of radiation delivered during the or each segment relative to patient anatomical data from the image, and subtract this from the mapped prescribed dose to create a new prescribed dose, and adjust the sub-doses and/or part sub-doses remaining to be delivered accordingly, and h) repeat the steps above from step c) to step g).

Such an apparatus allows an accurate fractional treatment to be planned quickly and easily, so that planned treatment can subsequently be carried out quickly and efficiently, in large part under automated control but overseen by a human operator, thus making efficient use of the system (which typically is in great demand and a scarce resource).

The apparatus may be further adapted, at the step of tracking the radiation delivered relative to patient anatomy in step g), to map the tracked radiation delivered against the anatomical data from the further image. The apparatus may comprise a collimator for variable collimation of the beam, the apparatus being further adapted to determine the collimation of the beam necessary to give the beam an outline matching the segments as determined in step d).

The apparatus may be further adapted, at the delivery step, step f) to adjust the beam intensity and/or duration of beam delivery. The further imaging device comprises a magnetic resonance image (MRI) device, an ultrasonic device or an electronic portal imaging device (EPID).

In a further aspect, the invention provides a radiotherapeutic apparatus for delivering a prescribed dose of radiotherapeutic radiation to a target region of patient tissue comprising a source for producing a directable beam of therapeutic radiation and a device for providing images depicting the relative positions of patient body parts and tissue types, wherein an image depicting patient anatomical data of at least the target region has been acquired and the prescribed dose has been mapped onto the image as the desired dose distribution to be achieved in the target region, the apparatus being adapted and configured to:

a) determine at least one beam angle corresponding to a direction from which the radiotherapeutic radiation is to be delivered from the source to the target region within an outline thereof, and for each beam angle create a mask defining a beam outline which substantially matches an outline of the target region as seen from each beam angle;

b) discretize the or each beam within its beam outline into a plurality of pencil beams;

c) for each beam angle carrying out a fluence optimisation process using pencil beam data from step b) and patient anatomical and target region data from the image to generate a distribution profile for a sub-dose at that beam angle, the separate sub-doses from all the angles in combination substantially equalling the prescribed dose;

d) segment each sub-dose distribution profile into separate segments, each segment comprising a plurality of pencil beams of matching fluence;

e) determine the efficiency of all of the segments;

f) deliver radiation in accordance with at least one of the most efficient segments of therapeutic radiation;

g) track the radiation delivered in step f) to calculate the amount and distribution of radiation delivered during the or each segment relative to patient anatomical data, subtract this from the mapped prescribed dose to create a new prescribed dose, and adjust the sub-doses and/or part sub-doses remaining to be delivered accordingly, and h) repeat the steps above, either from step a) to step g), or from step b) to step g)

One or more further images, each depicting patient anatomical data of at least the target region of the patient may be acquired, and used within the iterative loop. This use of further images improves the accuracy and efficiency of planning and effecting treatment, by taking into account the effects of each segment irradiation, through an iterative process involving one or both of the re-generation of the pencil beams, and the choice of new beam angles.

The invention also provides a method of planning the delivery of a prescribed dose of radiotherapeutic radiation to a target region of patient tissue with a radiotherapy system comprising a source for producing a directable beam of therapeutic radiation, the method comprising:

a) acquiring an image depicting patient anatomical data of at least the target region of the patient;

b) mapping the prescribed dose, being the desired dose distribution to be achieved in the target region, onto the image c) determining at least one beam angle corresponding to a direction from which the radiotherapeutic radiation is to be delivered from the source to the target region and for each beam angle creating a mask defining a beam outline which substantially matches an outline of the target region as seen from each beam angle;

d) discretizing the or each beam within its beam outline into a plurality of pencil beams;

e) for each beam angle carrying out a fluence optimisation process using pencil beam data from step d) and patient anatomical and target region data from step a) to generate a distribution profile for a sub-dose to be delivered at that beam angle, the separate sub-doses from all the angles in combination substantially equalling the prescribed dose;

f) segmenting each sub-dose distribution profile into segments, each segment comprising a plurality of pencil beams of matching fluence;

g) determining the efficiency of all the segments, and h) selecting the most efficient segment to be delivered first to the patient.

Such a method enables the fast and accurate planning of intensity-modulated radiotherapeutic treatment, particularly as a large proportion of the workload is carried out by the treatment planning computer, relieving the workload on the operator. It allows compensation for patient anatomy changes and enables radiation delivery immediately following the first calculated segment, and will lead to a fully adaptive intra-fraction planning system able to take into account patient anatomy updates during treatment.

In a different aspect, the invention further provides a method of delivering a prescribed dose of radiotherapeutic radiation to a target region of patient tissue with a radiotherapy system comprising a source for producing a directable beam of therapeutic radiation, the method comprising:

a) acquiring an image depicting patient anatomical data of at least the target region of the patient;

b) mapping the prescribed dose, being the desired dose distribution to be achieved in the target region, onto the image c) determining at least one beam angle corresponding to a direction from which the radiotherapeutic radiation is to be delivered from the source to the target region and for each beam angle creating a mask defining a beam outline which substantially matches an outline of the target region as seen from each beam angle;

d) discretizing the or each beam within its beam outline into a plurality of pencil beams;

e) for each beam angle carrying out a fluence optimisation process using pencil beam data from step d) and patient anatomical and target region data from step a) to generate a distribution profile for a sub-dose to be delivered at that beam angle, the separate sub-doses from all the angles in combination substantially equalling the prescribed dose;

f) segmenting each sub-dose distribution profile into segments, each segment comprising a plurality of pencil beams of matching fluence;

g) determining the efficiency of all of the segments;

h) delivering radiation in accordance with at least one of the most efficient segments of therapeutic radiation;

i) tracking the radiation delivered in step h) to calculate the amount and distribution of radiation delivered during the or each segment relative to patient anatomical data from step a), and subtracting this from the prescribed dose mapped in step b) to create a new prescribed dose, and adjusting the sub-doses and/or part sub-doses remaining to be delivered accordingly, and j) repeating the steps above from step e) to step i).

The invention also provides, in another aspect, a method of delivering a prescribed dose of radiotherapeutic radiation to a target region of patient tissue with a radiotherapy system comprising a source for producing a directable beam of therapeutic radiation and a device for providing images depicting the relative positions of patient body parts and tissue types, the method comprising:

a) acquiring an image depicting patient anatomical data of at least the target region of the patient;

b) mapping the prescribed dose, being the desired dose distribution to be achieved in the target region, onto the image;

c) determining at least one beam angle corresponding to a direction from which the radiotherapeutic radiation is to be delivered from the source to the target region within an outline thereof, and for each beam angle creating a mask defining a beam outline which substantially matches an outline of the target region as seen from each beam angle;

d) discretizing the or each beam within its beam outline into a plurality of pencil beams;

e) for each beam angle carrying out a fluence optimisation process using pencil beam data from step d) and patient anatomical and target region data from step a) to generate a distribution profile for a sub-dose at that beam angle, the separate sub-doses from all the angles in combination substantially equalling the prescribed dose;

f) segmenting each sub-dose distribution profile into separate segments, each segment comprising a plurality of pencil beams of matching fluence;

g) determining the efficiency of all of the segments;

h) delivering radiation in accordance with at least one of the most efficient segments of therapeutic radiation;

i) tracking the radiation delivered in step h) to calculate the amount and distribution of radiation delivered during the or each segment relative to patient anatomical data, subtracting this from the prescribed dose mapped in step b) to create a new prescribed dose, and adjusting the sub-doses and/or part sub-doses remaining to be delivered accordingly, and j) repeating the steps above, either from step c) to step i), or from step d) to step i).

As above, the use of further images improves the accuracy and efficiency of planning and effecting treatment, by taking into account the effects of each segment irradiation, through an iterative process involving one or both of the re-generation of the pencil beams, and the choice of new beam angles.

In all of the aspects of the invention, pencil beams of matching fluence may mean that contiguous or adjacent pencil beams having substantially the same fluence are placed in the same segment; alternatively it may be that contiguous or adjacent pencil beams having a fluence which is the same as or greater than a predetermined value are placed in the same segment. The terms "match", "matched" and "matching" used in this description and in the claims should be construed accordingly.

BRIEF DESCRIPTION OF THE DRAWINGS

An embodiment of the present invention will now be described by way of example, with reference to the accompanying figures in which;

FIG. 2 shows a part of a grid of pencil beams generated in performing the invention;

FIGS. 3a and 3b show a part of another grid of pencil beams generated in performing the invention to illustrate an alternative method for characterizing segment efficiency, and FIGS. 4a and 4b are schematic views of the iterative fluence optimisation process forming part of the process described herein.

DETAILED DESCRIPTION OF THE EMBODIMENTS

Figure 1:
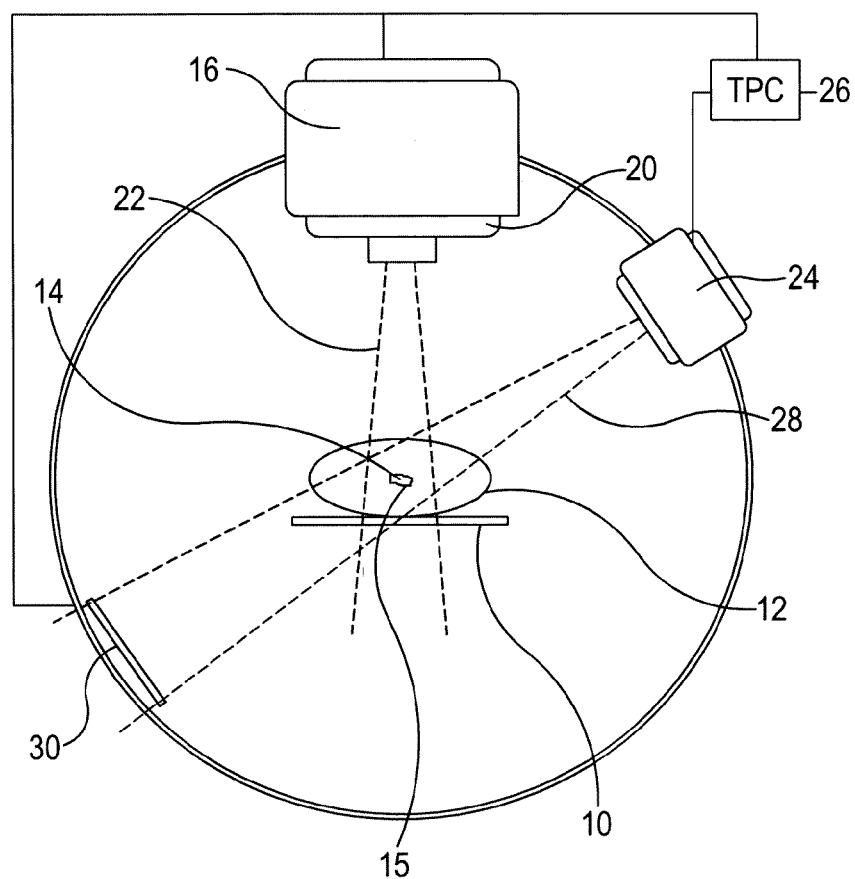
FIG. 1 shows a schematic layout of a conventional radiotherapy apparatus.

FIG. 1 shows a typical radiotherapy apparatus. A patient table 10 is provided, on which a patient 12 can be placed. Generally, the patient table is moveable (within limits) in any of its six degrees of freedom, i.e. three translational directions and three rotational directions, so as to place the relevant part of the patient that is to be treated at a specific location 14 within the treatment room, relative to the machine, known as the "isocentre". This may be made visible by a number of low-power lasers mounted at fixed locations and directed towards the isocentre 14. The patient table is ideally positioned so that the isocentre 14 lies within the outline of a target region 15, such as a cancerous tumour.

A radiation source 16 is mounted on a gantry (not visible) extending from a rotatable gantry 18. The radiation source may emit high-energy x-rays, or an electron beam, or a selectable choice of both, or another form of radiation. In one embodiment the source 16 is a linear accelerator. The rotatable gantry is usually set into a wall or other structure, so that the operating machinery can be concealed. The gantry 18 can rotate around a horizontal axis that passes through the isocentre 14, and the source 16 extends from the support 18 at a point offset from that horizontal axis but is directed towards the axis and the isocentre 14. Thus, as the gantry 18 rotates, the radiation source 16 illuminates the region around the isocentre 14 from all possible radial directions. This provides one way in which the apparatus limits the radiation dose applied to healthy tissue while maintaining the dose applied to the tumour or other lesion being treated; the lesion (or relevant part of it) can be exposed during the entirety of the treatment, but the surrounding tissue will only be exposed when directly in line with the beam.

Another way of limiting the dose applied to healthy tissue is the use of collimators for the radiation beam. These are housed as a collimator set 20 integrated with the radiation source 16 and acting on the beam 22 it produces so as to limit its lateral extent. They comprise two pairs of collimators, each acting in mutually transverse directions so as to limit the beam in all directions. There is usually a block collimator, comprising a pair of collimating sections which are moveable back and forth in an x direction and have a flat front face substantially parallel with the y direction. By moving the blocks back and forth, the beam can be limited in the x direction as desired.

The second pair of collimators are multi-leaf collimators (MLCs). These comprise two mutually opposed banks of leaves, each leaf being extendable back and forth in the y direction and being relatively long in the y direction so as to allow it to reach across a significant proportion of the beam width, relatively deep in the z direction so as to allow it to attenuate the beam significantly, and relatively narrow in the x direction so as to allow a good resolution. By moving individual leaves to a desired position, each bank of leaves as a whole can present a front edge that takes up substantially any shape.

Between the two collimators, the beam can be delimited to substantially any required shape, with the block collimator defining the lateral extent of the shape in the x direction and the multi-leaf collimator defining the remaining part of the shape. In combination with the rotational movement of the radiation source 16, the collimators allow a complex three-dimensional dose distribution to be built up within the patient, in line with the prescription developed by the patient's clinician. In standard practice oncologists prescribe a radiation dose that allows a certain percentage of volume in healthy tissue to be sacrificed in order to make sufficient progress in treating the adjacent target region, such as a cancerous tumour. A typical dose might be, for example, that the target region is to receive a radiation dose of 80 Gy (where "Gy" is the shorthand for "Gray" the international unit for radiation dose absorption), whilst no more than 30% volume of an adjacent organ can exceed a radiation dose of 20 Gy. The prescribed dose distribution results from multiple beams of different shapes and different directions of arrival which are produced by varying the angle at which the source irradiates the patient, the dose rate of radiation emitted from the source, and the shape outlined by the collimator during treatment, either stepwise or continuously. The following description will describe the invention in terms of a stepwise arrangement, where a number of discrete angles are chosen from which to deliver the radiotherapeutic radiation; those skilled in the art will appreciate the changes required to operate in a continuous fashion, with the apparatus adjusting as the radiation source 16 moves continuously around the isocentre 14.

To calculate the necessary rotations, dose rates, and collimator shapes that will deliver a desired dose distribution, a "treatment planning computer" (TPC) 26 is usually employed. This receives the prescribed dose in the form of a dose distribution, which will normally be a three-dimensional map showing areas which must receive a specified dose of radiation, such as the lesion itself, areas in which the dose should be minimised to the extent possible, and areas where substantially no radiation or less than a specified dose must be delivered, such as sensitive structures including the bowels, optic nerves, spinal cord, and the like. It also receives a set of "machine constraints", which detail the nature of the apparatus including the geometry of the beam and the collimators, maximum dose rates and maximum rotation speeds, etc. An algorithm is then applied to produce a "treatment plan" comprising detailed instructions for the radiotherapy apparatus in terms of required rotation speeds, dose rates, MLC shapes etc. and their variation with time. The details of this algorithm are not relevant to the present invention and are known per se; they are discussed in WO2002/049044, for example.

Also shown in FIG. 1 is a source of imaging radiation 24, mounted so as to rotate around the isocentre 14 and to generate a beam of imaging radiation 28 towards the isocentre 14, so that the beam 28 passes through the patient 12 and is picked up by an imaging device 30, which is usually arranged to rotate with the imaging source 24 and fixedly spaced directly opposite, at 180 degrees. The imaging source 24 is located in a known position relative to the radiation source 16, so that the images of the patient's anatomy and of the target region 15 acquired by device 30 can be correlated with the radiation emitted by the source 16. The radiation source 16 and the collimator set 20, the imaging source 24 and the imaging device 30 and their respective control and movement mechanisms (not shown) are all operatively connected to the TPC 26, which is also connected (at 26) to other data processing and/or storage devices (not shown) if these are required to assist the TPC and to a user interface such as a computer and linked display (not shown) for the operator to control the system so as to deliver the prescribed dose to the target region.

In the practice of the invention, an image (which is preferably three-dimensional, obtained such as by acquiring a succession of different images of the target region from different angles) is first acquired of the target region 15 (though patient tissue surrounding that region will often also be imaged, so that the effects of radiation on that surrounding or adjacent, non-target tissue can be controlled and the radiation delivered thereto can be limited to whatever level is appropriate (which may be nil in the case of critically sensitive tissues or organs, or some level above that but below the level to be delivered to the target region for other, less-sensitive tissues)). This image is then fed into the TPC 26. In order to reduce the dose to non-targeted organs during radiotherapy, it is advantageous to image the region of the body to be treated as close to the time of treatment as possible, however in practice the image may be acquired in advance, and may use some other imaging system than the imaging source 24.

With the patient positioned as shown in FIG. 1, anatomical data of the target region 15 (and, optionally, of surrounding/adjacent tissue) which is derived from and depicted in the 3D image is loaded into the TPC 26. The TPC, directed by the operator, maps the prescribed dose onto the target region so as to specify the prescribed or desired dose distribution to be achieved in the target region. The TPC 26 then performs a beam angle optimisation, i.e. calculates the beam angles—the positions around the isocentre from which the radiotherapy beam 22 is to be directed at the target region; this calculation takes into account the nature and location of the target region, of the surrounding patient anatomy, and the radiation delivery characteristics attainable by the radiation source 16. Having made this calculation, the TPC then defines a mask which defines the outline of the beam to be delivered from each beam angle; the beam outline at a particular beam angle corresponds to the outline of the target region as seen from that beam angle (or, in some applications, it may correspond to a smaller area than the outline of the target region but falling within the outline of the target region). The TPC also calculates the sub-dose of radiation to be delivered at each beam angle (where the combined sub-doses from every beam angle add up to, or approach but do not exceed, the prescribed dose distribution.

The next step is the discretisation of each beam at each beam angle, to generate a plurality of hypothetical pencil beams, sometimes known as beamlets; these are straight-line pathways, usually of a conical or cylindrical shape, with a very small cross-sectional area, which are used for predicting the behaviour and/or characteristics of the larger beam of radiation under different circumstances. This known discretisation process is carried out by the known Monte Carlo method, the known collapsed cone method, or any other suitable discretising engine. The beams having been discretised into pencil beams, fluence optimisation is performed (any known fluence optimisation implementation may be used, though the faster ones are preferred if the invention is to be iterative), using the pencil beam data from the discretisation process and anatomical data of the patient and the target region from the image; this results in the generation of a distribution profile for the sub-dose at each beam angle, or a first fluence optimisation. The first fluence optimization is regarded as the optimal fluence distribution for the rest of the algorithm from which the sub-dose that each segment delivers will be subtracted. In the case of a real-time imaging modality that provides the algorithm with anatomy updates between irradiations, each time some anatomy deformations occur, this optimal reference fluence distribution will be substituted by the new fluence calculated on the updated anatomy as will be described.

The next step is segmentisation of the beam at each beam angle; pencil beams of matching fluence are grouped, in shapes which the radiation source 16 is capable of delivering (for example, if a group of pencil beams of matching fluence forms a shape that the MLC is incapable of replicating, that segment would not be acceptable and the segmentation process would have to be restarted). The matching of pencil beams could require them to be of equal fluence, alternatively a degree of tolerance may be exercised in deeming the fluence of separate pencil beams as "matched". Alternatively, the matching of pencil beams could mean that pencil beams having a fluence equal to or greater than a predetermined fluence are matched (i.e. placed in the same segment). Any type of fast segmentation can be used. In one implementation the segmentation is done as follows: the beam's fluence is split into 1000 discrete intensity levels, and each pencil beam is given an intensity value between 0-1000. The pencil beams are then grouped into segments based on their location and intensity level, and whether or not they would be physically deliverable by the radiotherapeutic apparatus. Each segment is then characterized by its efficiency which is the result of the multiplication between the segment's area and its intensity level—however different objective functions could be used to describe the efficiency of each segment. This is illustrated in FIG. 2, which shows a 5×5 grid 35 of part of a fluence optimisation map, where each cell corresponds to a pencil beam and indicates the radiation dose to be delivered to the target region thereby. As can be seen, there is a group of 4 cells towards the centre of the grid, each of which has a fluence of 10 Gy. There is a second group of 3 cells in a line along the top edge of the grid each of which has a fluence of 7 Gy, and a third group of 6 cells to the right hand side of the grid, each of which has a fluence of 4 Gy. Using the above calculation, the efficiency of the first group is 40, of the second group 21, and of the third group 24; the first group is therefore the most efficient, followed by the third and then the second. The TPC 26 ranks these in order of efficiency and then chooses the most efficient as the first segment to be delivered at that beam angle. Alternatively, a predetermined fluence level of 7 could be applied, and a group formed of all those contiguous cells having a fluence equal to or greater than 7—as shown by the outlined group of ten cells 37. Because a fluence level has been predetermined in forming this group, its efficiency will be the predetermined fluence level (or segment intensity) multiplied by the area (i.e. the number of cells in the group). Other groups of "matched" fluence would then be formed (using either of the above-described methods), and then the groups ranked in order of efficiency as described.

FIGS. 3a and 3b illustrate an alternative process for calculating segment efficiency; while every segment has a single intensity level, the beamlets or cells that form it might have different intensity levels, and by taking this variable into account, the segment selection process has more information about the contribution of its beamlets to the overall intensity distribution. FIGS. 3a and 3b show a 3×3 grid 39 of part of a fluence optimisation map, where each cell corresponds to a pencil beamlet and indicates the radiation dose to be delivered to the target region thereby, as in FIG. 2. In FIG. 3a, a segment 41 of 6 cells is shown shaded; the segment 41 has been chosen for cells with an intensity level of 5 or greater; FIG. 3b shows a segment 43 of 3 cells which has been chosen for cells with an intensity level of 9 or greater. Using the method described above in connection with FIG. 2 for determining segment efficiency, where segment efficiency equals intensity level multiplied by the area having that intensity level, the efficiency of segment 41 would be 5×6, or 30. By the same method, the intensity of segment 43 would be 27; the above method would therefore rank the segment 41 as the most efficient. If the segment is qualified by the average cell (or beamlet) intensity, then the average beamlet intensity in segment 41 is 7 ((3×9+3×5)/6) and the average beamlet intensity in segment 43 is 9. Utilising this average beamlet intensity to qualify the segment efficiency obtained by multiplying the intensity level by the area (i.e. multiplying the efficiency derived above in connection with FIG. 2 by the average beamlet intensity) gives a qualified efficiency for segment 41 of 210 (5×6×7) and a qualified segment efficiency for segment 43 of 243 (9×3×9); using this qualified efficiency, smaller segment 43 would be deemed more efficient than larger segment 41. Using this qualified efficiency provides a more balanced comparison between large regions of moderate intensity and smaller high intensity regions than the method of FIG. 2. The method of FIG. 2 made the calculation in some cases difficult (e.g. cases with boost dose in some parts of the targets) as it constantly favours larger segments and thus could fail to deliver part of the dose in the high dose regions of the targets.

At this point, once the segment efficiencies have been determined, the dose which will actually be delivered in this segment is calculated (this dose is slightly different than assumed in the segmentation step above as the machine parameters were not obeyed at that point (with the exception of whether or not a segment shape could be created by the collimation apparatus), so no leaf transmission and penumbra effects etc. were accounted for). In one implementation the MC verify (trade mark) engine is used for this dose calculation, but any "good" dose engine that accounts for the machine parameters would also work).

The system can then deliver the radiation in that segment (either the most efficient group only or, to speed up the overall process, several of the most efficient, in order of efficiency). During delivery, or immediately thereafter, a further image may be acquired of the patient target region 15; this image is taken by the imaging source 24 and device 30, and is used to determine the location of the target region 15, which may have shifted and/or deformed since the first image was acquired and the end of this sub-dose irradiation. This allows the delivered sub-dose to be accurately mapped onto the patient anatomy. If no further image is acquired, then the delivered sub-dose is mapped onto the original image.

The system then subtracts the delivered sub-dose from the first fluence optimisation, to generate a new fluence optimisation, and the process can be repeated. If a further image has been acquired and this is taken into account in mapping of the delivered sub-dose, then the system can return to the step of discretisation into pencil beams, or to the step of beam angle optimisation, which cumulatively improve the accuracy of radiation delivery, but at the cost of increased data processing.

FIG. 4 illustrates this subtraction process schematically. FIG. 4a shows the prescribed sub-dose distribution at a single beam angle (with fluence illustrated along the vertical axis, and location along the horizontal) as a curve 45, the area below which represents the radiation yet to be delivered to complete the prescribed dose, or sub-dose for that beam angle. The area below curve 45 is divided by vertical lines into segments 47, 49, 51 as described above. For the sake of example, segment 51 is the most efficient segment, and it can be delivered as shown by the shaded area 51a—the fluence of the beams in each segment being the same, the shaded area is rectangular as shown, and preferably at no point exceeds the prescribed dose as shown by curve 45, so as not to deliver more radiation than was originally prescribed. It will be apparent that there is an amount of sub-dose which has not been delivered (represented by the unshaded area 51b in segment 51). The undelivered sub-dose may arise because the prescribed dose varies over a segment whilst the radiation fluence level is substantially constant, and/or because the fluence level of the radiation is not equal over the entire area of the irradiated segment. This undelivered radiation (unshaded area 51b) is carried over into the new fluence optimisation as shown in FIG. 4b. In the next step of the process, the fluence optimisation of FIG. 4b is used as the starting basis, and it will be understood that now the radiation remaining to be delivered in segment 51b is, as shown, clearly less efficient than either of segments 47 and 49, so one of those segments, or a segment from another beam angle of greater efficiency, will be the next to be delivered. In this way, the prescribed dose is approached or achieved by an iterative process, with the radiation remaining to be delivered decreasing by stages as successive segments are delivered. In illustrative terms, the curve 45 for each beam angle is gradually lowered towards the horizontal axis until it is beyond the capacity of the radiation source, or inefficient in terms of the time taken for the treatment, for the process to continue. A practical point at which to cease the treatment at any one beam angle is when there is a particular and predetermined maximum height of the curve 45 remaining after multiple fluence optimisations. If the process involves further imaging as described above, there can be more confidence in the accuracy with which radiation has been delivered than where only the initial image is used, so the threshold for ceasing operation (i.e. the maximum height of the curve 45) can be lower for the former than for the latter (the "first threshold" and "second threshold" of the claims). An alternative way of deciding when to cease the process would be when the total sub-dose of the next most efficient segment to be delivered is less than a predetermined sub-dose (the "predetermined dose threshold" of the claims). A yet further way of deciding when to terminate the process could be when a certain number of segments has been calculated.

EXAMPLE

Method: Pencil beams were generated for each beam angle of the treatment and a fluence optimization performed. The pencil beams, together with the patient anatomy and the above optimal fluence form the input of the algorithm. During each of a number of iterations the following steps were performed: A fluence optimization was carried out, and each beam's fluence then split to discrete intensity levels. Deliverable segments were calculated for each of these. Each segment's area was multiplied by its intensity to determine its efficiency. The most efficient segment among all beams was then chosen to deliver a part of the calculated fluence, and the dose that would be delivered by this segment calculated. This delivered dose was then subtracted from the remaining dose. This loop was repeated until 90% of the dose had been delivered and a final segment weight optimization was performed to reach full convergence.

Results: The algorithm was tested in several prostate cases. All prostate cases used in this work were planned on a grid with 3 mm×3 mm×3 mm spacing using seven beams and a boost dose region. The following clinical constraints were to be met from the sequenced plan: more than 99% of the PTV should receive 66.5 Gy, more than 99% of the EBV should receive 73.15 Gy, at most 50% of the Rectum can receive 50 Gy, at most 5% of the Rectum can receive 72 Gy, at most 2 cc of the planning organ at risk volume (PRV) Rectum can receive 77 Gy, at most 10% of the Bladder can receive 72 Gy, at most 1 cc of the Bladder can receive 80 Gy and the average dose delivered to the Sphincter should be less than 37 Gy. The test yielded results that met all clinical constraints. Quality assurance was also performed on Delta4 and film phantoms for one of these prostate cases, and received clinical acceptance after passing both gamma analyses within the 3%/3 mm criteria.

In practice it is likely that a fractional treatment will be stopped leaving a small amount of dose undelivered, because the next most efficient segment to be delivered is less than the predetermined dose threshold, or because the "undelivered dose" is distributed such that it cannot be delivered due to machine or time constraints or because delivery might exceed the dose applied to non-targeted tissue. This undelivered dose and its distribution can be recorded, and/or input to the treatment planning computer, so as to be added to the prescribed dose for the next fractional treatment. Over a course of treatment of several fractions, this way of compensating for undelivered doses from fraction to fraction can more accurately and quickly converge on the desired overall, or cumulative, treatment plan. Because there is likely to be inter-fractional movement in the majority of cases, which movement will be registered in the imaging step prior to the next fractional treatment, the treatment plan for the next fraction is likely to differ from the previous treatment plan, in terms of at least one of the beam angles, beam-angle-optimisation, fluence optimisation and segmentation; these differences, over several fractional treatments, are able cumulatively to take account of those factors which led to the undelivered dose in one or more preceding fractions. This improves the efficiency of treatment for a patient as, instead of painstakingly and time-consumingly trying to complete the last elements of undelivered dose during one fractional treatment, the undelivered dose from that fraction can be factored into the next fractional treatment, and/or into subsequent fractional treatments.

It will of course be understood that many variations may be made to the above-described embodiment without departing from the scope of the present invention. For example, the system can deliver all the segments at one beam angle before moving on to deliver those at another beam angle, however it is generally more efficient for consecutively delivered segments to originate from different beams. This takes advantage of the multiple angles that are available, and allows the radiation source to operate in a roughly linear fashion, e.g. from a high radiation intensity to a low intensity as the segments are delivered—albeit at the cost of the time required to move between beam angles.

The system illustrated in the drawings has a megavolt system or kilovolt imaging system, however any type of imaging system can be used, such as an ultrasound or MRI system. The invention is particularly advantageous for use with an MRI scanner, in an MRL system, due to its ability to provide rapid, accurate and very timely images, and intra-fraction images without increasing the radiation dose to the patient.

The invention has been described above and defined in the claims in respect of a radiation source which is rotatable around the patient on a gantry or such like, however it is equally practicable with an apparatus in which, rather than moving in this way, the radiotherapeutic radiation source is mounted onto a movable robot arm so as to direct radiation from almost any location and/or angle towards the patient target region (one such device is sold under the trade mark Cyberknife); it is intended that the appended claims also encompass just such arrangements, and so the term "beam angle" should be interpreted throughout this application be interpreted accordingly.

Reference is made above to the use of 3D images; the images may be 4D, as known in the art, so as to take account of intra-fraction movements such as the cyclical movement of a patient's anatomy due to breathing, heartbeat, digestive processes, etc.

Some embodiments of the invention can be implemented in whole or in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network. The series of computer instructions embodies all or part of the functionality previously described herein with respect to the system. Those skilled in the art should appreciate that such computer instructions can be written in any suitable programming language, for use with any computer architecture or operating system. Furthermore, such instructions may be stored in any memory device, such as semiconductor, magnetic, optical or other memory devices, and may be transmitted using any communications technology, such as optical, infrared, microwave, or other transmission technologies. Such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). It will of course also be understood that some embodiments of the invention will be implemented as a combination of both software (e.g., a computer program product) and hardware. Some embodiments may be easily retro-fitted to existing radiotherapy systems, either as software updates alone, or as a combination of new software and hardware (including both computer hardware and other, non-computer apparatus items.

Furthermore, where different variations or alternative arrangements are described above, it should be understood that embodiments of the invention may incorporate such variations and/or alternatives in any suitable combination.

The invention claimed is:

1. A radiotherapeutic apparatus for delivering a prescribed dose of radiotherapeutic radiation to a target region of patient tissue, wherein an image depicting patient anatomical data of at least the target region has been acquired and the prescribed dose has been mapped onto the image as a desired dose distribution to be achieved in the target region, the radiotherapeutic apparatus comprising:
   a source configured to produce a directable beam of therapeutic radiation; and
   a controller configured to:
      determine at least one beam angle corresponding to a direction from which the radiotherapeutic radiation is to be delivered from the source to the target region;
      create a mask for each beam angle, the mask defining a beam outline substantially matching an outline of the target region as seen from each beam angle;
      discretize each beam within its beam outline into a first plurality of pencil beams;
      perform a fluence optimisation process for each beam angle using pencil beam data from the first plurality of pencil beams, the patient anatomical data, and the target region data to generate a distribution profile for a sub-dose to be delivered at that beam angle, wherein sub-doses from each beam angle in combination substantially equal the prescribed dose;
      segment the sub-dose distribution profile into segments, each segment comprising a second plurality of pencil beams of matching fluence;
      determine the efficiency of the segments by splitting the beam's fluence into a plurality of discrete intensity levels and splitting the cross-sectional area of the segment into discrete sections, so as to derive the efficiency as a function of the discrete intensity level and the area of a section;
      deliver radiation in accordance with at least one of the most efficient segments of therapeutic radiation;
      track the delivered radiation to calculate the amount and distribution of radiation delivered during each segment relative to the patient anatomical data;
      subtract the calculated amount and distribution of radiation from the mapped prescribed dose to create a new prescribed dose; and
      adjust the sub-doses remaining to be delivered according to the new prescribed dose.

2. The apparatus according to claim 1, the controller being further configured to:
   determine if the new prescribed dose is less than a first threshold value; and
   repeat the steps performed by the radiotherapeutic apparatus if the new prescribed dose is determined not to be less than the first threshold value.

3. The apparatus according to claim 2, the controller being further configured to:
   determine the part of the prescribed dose and its distribution which remains to be delivered when the new prescribed dose is less than a first threshold value; and
   record the determined part for incorporation in a treatment plan for delivering in a subsequent prescribed dose.

4. A radiotherapeutic apparatus for delivering a prescribed dose of radiotherapeutic radiation to a target region of patient tissue, comprising:
   a source configured to produce a directable beam of therapeutic radiation;
   an imaging device configured to provide images depicting the relative positions of patient body parts and tissue types, wherein an image depicting patient anatomical data of at least the target region has been acquired and the prescribed dose has been mapped onto the image as a desired dose distribution to be achieved in the target region; and
   a controller configured to:
   determine at least one beam angle corresponding to a direction from which the radiotherapeutic radiation is to be delivered from the source to the target region within an outline
   create a mask for each beam angle, the mask defining a beam outline substantially matching an outline of the target region as seen from each beam angle;
   discretize each beam within its beam outline into a first plurality of pencil beams;
   perform a fluence optimisation process for each beam angle using pencil beam data from the first plurality of pencil beams, the patient anatomical data, and the target region data to generate a distribution profile for a sub-dose at that beam angle, wherein sub-doses from each beam angle in combination substantially equal the prescribed dose;
   segment the sub-dose distribution profile into separate segments, each segment comprising a second plurality of pencil beams of matching fluence;
   determine the efficiency of the segments by splitting the beam's fluence into a plurality of discrete intensity levels and splitting the cross-sectional area of the segment into discrete sections, so as to derive the efficiency as a function of the discrete intensity level and the area of a section;

deliver radiation in accordance with at least one of the most efficient segments of therapeutic radiation;

track the delivered radiation to calculate the amount and distribution of radiation delivered during each segment relative to the patient anatomical data;

subtract the calculated amount and distribution of radiation from the mapped prescribed dose to create a new prescribed dose; and adjust the sub-doses remaining to be delivered according to the new prescribed dose.

5. The apparatus according to claim 4, wherein the imaging device acquires a further image depicting patient anatomical data of at least the target region of the patient after adjusting the sub-doses remaining to be delivered.

6. The apparatus according to claim 5, the controller being further configured to:

map the tracked radiation delivered against the anatomical data from the further image.

7. The apparatus according to claim 5, wherein the imaging device comprises a magnetic resonance image (MRI) device, an ultrasonic device or an electronic portal imaging device (EPID).

8. The apparatus according to claim 4, the controller being further configured to:

determine if the new prescribed dose is less than a first threshold value; and repeat the steps performed by the radiotherapeutic apparatus if the new prescribed dose is determined not to be less than the first threshold value.

9. The apparatus according to claim 4, the controller being further configured to:

determine if the total sub-dose of the next most efficient segment to be delivered is less than a predetermined dose threshold; and repeat the steps performed by the radiotherapeutic apparatus if the total sub-dose of the next most efficient segment to be delivered is determined not to be less than the predetermined dose threshold.

10. The apparatus according to claim 4, comprising a collimator for variable collimation of the beam, the controller being further configured to determine a collimation of the beam necessary to give the beam an outline matching the determined segments.

11. The apparatus according to claim 10, wherein segmenting the sub-dose distribution profile further comprises the controller configured to:

group pencil beams of matching fluence according to a beam having an outline which the collimator is capable of producing, and discard any groups having an outline which the collimator is incapable of producing.

12. The apparatus according to claim 11, the controller being further configured to:

choose at least one segment, after determining the efficiency of the segments, to calculate the level and distribution of radiation which will actually be delivered in the segment by the radiotherapeutic apparatus, and use the calculated level and distribution for the subtraction from the mapped prescribed dose to create a new prescribed dose.

13. The apparatus according to claim 4, wherein the efficiency is qualified by the average intensity within the area.

14. The apparatus according to claim 4, wherein delivering radiation in accordance with at least one of the most efficient segments includes adjusting the beam intensity or the duration of beam delivery.

15. The apparatus according to claim 4, wherein discretizing the beam further includes using a Monte Carlo algorithm or a collapsed cone algorithm.

16. A method of planning delivery of a prescribed dose of radiotherapeutic radiation to a target region of patient tissue with a radiotherapy system comprising a source for producing a directable beam of therapeutic radiation, the method comprising:

acquiring an image depicting patient anatomical data of at least the target region of the patient;

mapping the prescribed dose onto the image, the prescribed dose being the desired dose distribution to be achieved in the target region;

determining at least one beam angle corresponding to a direction from which the radiotherapeutic radiation is to be delivered from the source to the target region;

creating a mask for each beam angle, the mask defining a beam outline substantially matching an outline of the target region as seen from each beam angle;

discretizing each beam within its beam outline into a first plurality of pencil beams;

perform a fluence optimisation process for each beam angle using pencil beam data from the first plurality of pencil beams, the patient anatomical data, and the target region data to generate a distribution profile for a sub-dose to be delivered at that beam angle, wherein sub-doses from each beam angle in combination substantially equal the prescribed dose;

segmenting the sub-dose distribution profile into segments, each segment comprising a second plurality of pencil beams of matching fluence;

determining the efficiency of the segments by splitting the beam's fluence into a plurality of discrete intensity levels and splitting the cross-sectional area of the segment into discrete sections, so as to derive the efficiency as a function of the discrete intensity level and the area of a section; and selecting the most efficient segment to be delivered first to the patient.

17. The method according to claim 16, wherein the radiotherapy system comprises a collimator configured for variable collimation of the beam, the method further comprising:

determining the collimation of the beam necessary to give the beam an outline matching the segments.

18. The method according to claim 16, wherein the step of segmenting each sub-dose distribution profile comprises:

grouping pencil beams of matching fluence according to a beam having an outline which the collimator is capable of producing, and discarding any groups having an outline which the collimator is incapable of producing.

19. The method according to claim 16, further comprising qualifying the efficiency by the average intensity within the area.

20. The A method according to claim 16, wherein discretizing the beam into a plurality of pencil beams comprises using a Monte Carlo algorithm or a collapsed cone algorithm.

21. The method according to claim 16, wherein the image comprises anatomical data of patient tissue outside the target region.

22. The method according to any of claim 16, further comprising:
planning the prescribed dose so as to incorporate into the treatment plan for a fractional treatment parts of a dose and of its distribution from a previous prescribed dose.

23. A method of delivering a prescribed dose of radiotherapeutic radiation to a target region of patient tissue with a radiotherapy system comprising a source for producing a directable beam of therapeutic radiation, the method comprising:
acquiring an image depicting patient anatomical data of at least the target region of the patient;
mapping the prescribed dose onto the image, the prescribed dose being the desired dose distribution to be achieved in the target region;
determining at least one beam angle corresponding to a direction from which the radiotherapeutic radiation is to be delivered from the source to the target region;
creating a mask for each beam angle, the mask defining a beam outline substantially matching an outline of the target region as seen from each beam angle;
discretizing each beam within its beam outline into a first plurality of pencil beams;
perform a fluence optimisation process for each beam angle using pencil beam data from the first plurality of pencil beams, the patient anatomical data, and the target region data to generate a distribution profile for a sub-dose to be delivered at that beam angle, wherein sub-doses from each beam angle in combination substantially equal the prescribed dose;
segmenting the sub-dose distribution profile into segments, each segment comprising a second plurality of pencil beams of matching fluence;
determining the efficiency of the segments by splitting the beam's fluence into a plurality of discrete intensity levels and splitting the cross-sectional area of the segment into discrete sections, so as to derive the efficiency as a function of the discrete intensity level and the area of a section;
delivering radiation in accordance with at least one of the most efficient segments of therapeutic radiation;
tracking the delivered radiation to calculate the amount and distribution of radiation delivered during each segment relative to the patient anatomical data;
subtracting the calculated amount and distribution of radiation from the mapped prescribed dose to create a new prescribed dose; and
adjusting the sub-doses remaining to be delivered according to the new prescribed dose.

24. The method according claim 23, wherein delivering radiation comprises adjusting the radiotherapy system so as to vary the beam intensity or the duration of beam delivery.

25. The method according to claim 23, wherein discretizing the beam into a plurality of pencil beams comprises using a Monte Carlo algorithm or a collapsed cone algorithm.

26. A method of delivering a prescribed dose of radiotherapeutic radiation to a target region of patient tissue with a radiotherapy system comprising a source for producing a directable beam of therapeutic radiation and an imaging device for providing images depicting the relative positions of patient body parts and tissue types, the method comprising the following steps:
acquiring an image depicting patient anatomical data of at least the target region of the patient;
mapping the prescribed dose onto the image, the prescribed dose being the desired dose distribution to be achieved in the target region;
determining at least one beam angle corresponding to a direction from which the radiotherapeutic radiation is to be delivered from the source to the target region within an outline of the target region;
creating a mask for each beam angle, the mask defining a beam outline substantially matching an outline of the target region as seen from each beam angle;
discretizing each beam within its beam outline into a first plurality of pencil beams;
perform a fluence optimisation process for each beam angle using pencil beam data from the first plurality of pencil beams, the patient anatomical data, and the target region data to generate a distribution profile for a sub-dose at that beam angle, wherein sub-doses from each beam angle in combination substantially equal the prescribed dose;
segmenting the sub-dose distribution profile into separate segments, each segment comprising a second plurality of pencil beams of matching fluence;
determining the efficiency of the segments by splitting the beam's fluence into a plurality of discrete intensity levels and splitting the cross-sectional area of the segment into discrete sections, so as to derive the efficiency as a function of the discrete intensity level and the area of a section;
delivering radiation in accordance with at least one of the most efficient segments of therapeutic radiation;
tracking the delivered radiation to calculate the amount and distribution of radiation delivered during each segment relative to the patient anatomical data;
subtracting the calculated amount and distribution of radiation from the mapped prescribed dose to create a new prescribed dose; and
adjusting the sub-doses remaining to be delivered according to the new prescribed dose.

27. The method according to claim 26, further comprising:
acquiring a further image depicting patient anatomical data of at least the target region of the patient after adjusting the sub-doses remaining to be delivered.

28. The method according to claim 27, further comprising:
determining if the new prescribed dose is less than a first threshold value; and
ceasing the treatment if the new prescribed dose is less than a first threshold value.

29. The method according to claim 28, further comprising:
determining if the new prescribed dose is less than a second threshold value; and
ceasing the treatment if the new prescribed dose is less than a second threshold value.

30. The method according to claim 27, further comprising:
determining if the total sub-dose of the next most efficient segment to be delivered is less than a predetermined dose threshold; and
repeating the steps performed by the radiotherapy system if the total sub-dose of the next most efficient segment to be delivered is determined not to be less than the predetermined dose threshold.

31. The method according to claim 27, wherein the image comprises anatomical data of patient tissue outside the target region.

32. The method according to claim 26, further comprising:
- determining the part of the prescribed dose and its distribution which remains to be delivered when the new prescribed dose is less than a first threshold value; and
- recording the determined part for incorporation in a treatment plan for delivery in a subsequent prescribed dose.

33. The method according to claim 32, further comprising:
- choosing at least one segment, after determining the efficiency of the segments, to calculate the level and distribution of radiation which will actually be delivered in the segment by the radiotherapy system, and
- using the calculated level and distribution for the subtraction from the mapped prescribed dose to create a new prescribed dose.

34. A method according to claim 27, further comprising: mapping the tracked radiation delivered against the anatomical data from the further image.

35. The method according to claim 26, wherein the radiotherapy system comprises a collimator configured for variable collimation of the beam, the method further comprising:
- determining the collimation of the beam necessary to give the beam an outline matching the segments.

36. The method according to claim 35, wherein determining the necessary collimation of the beam is carried out after creating the mask.

37. The method according to claim 35, wherein segmenting the sub-dose distribution profile comprises:
- grouping pencil beams of matching fluence according to a beam having an outline which the collimator is capable of producing, and
- discarding any groups having an outline which the collimator is incapable of producing.

38. The method according to claim 26, wherein the further image is a magnetic resonance image (MRI), an ultrasound image or an image from an electronic portal imaging device (EPID).

* * * * *

UNITED STATES PATENT AND TRADEMARK OFFICE
CERTIFICATE OF CORRECTION

PATENT NO. : 9,919,166 B2  
APPLICATION NO. : 15/301887  
DATED : March 20, 2018  
INVENTOR(S) : Charis Kontaxis et al.

Page 1 of 1

It is certified that error appears in the above-identified patent and that said Letters Patent is hereby corrected as shown below:

Claim 20, Column 18, Line 64, "The A method according to" should read -- The method according to --.

Claim 22, Column 19, Line 4, "method according to any of claim 16" should read -- method according to claim 16 --.

Signed and Sealed this  
Fourteenth Day of August, 2018

Andrei Iancu  
*Director of the United States Patent and Trademark Office*